(12) United States Patent
Feyler

(10) Patent No.: US 7,646,001 B2
(45) Date of Patent: Jan. 12, 2010

(54) FAKE ID FINDER

(76) Inventor: David Michael Feyler, 20 Baker St., Westwood, MA (US) 02090

( * ) Notice: Subject to any disclaimer, the term of this patent is extended or adjusted under 35 U.S.C. 154(b) by 0 days.

(21) Appl. No.: 12/075,760

(22) Filed: Mar. 12, 2008

(65) Prior Publication Data

US 2008/0224069 A1 Sep. 18, 2008

Related U.S. Application Data

(60) Provisional application No. 60/906,377, filed on Mar. 12, 2007.

(51) Int. Cl.
*G01N 21/64* (2006.01)

(52) U.S. Cl. ................................... 250/461.1

(58) Field of Classification Search .............. 250/461.1; 359/350
See application file for complete search history.

(56) References Cited

U.S. PATENT DOCUMENTS

| | | | | |
|---|---|---|---|---|
| 3,725,694 | A | * | 4/1973 | D'Amato et al. .......... 250/485.1 |
| 5,434,398 | A | * | 7/1995 | Goldberg .................... 235/380 |
| 5,668,377 | A | * | 9/1997 | Erickson ................. 250/504 R |
| 5,874,742 | A | * | 2/1999 | Romano .................. 250/461.1 |
| 2007/0127235 | A1 | * | 6/2007 | Cooper et al. ............... 362/217 |

* cited by examiner

*Primary Examiner*—David P Porta
*Assistant Examiner*—Kiho Kim
(74) *Attorney, Agent, or Firm*—Lambert & Associates; Adam J. Bruno; Gary E. Lambert

(57) ABSTRACT

A device for the identification of security features on an identification card, wherein the device includes a housing having a pair of circuit boards, a pair of light-emitting diodes and a magnification apparatus to allow for operation during both daylight and darkness.

16 Claims, 14 Drawing Sheets

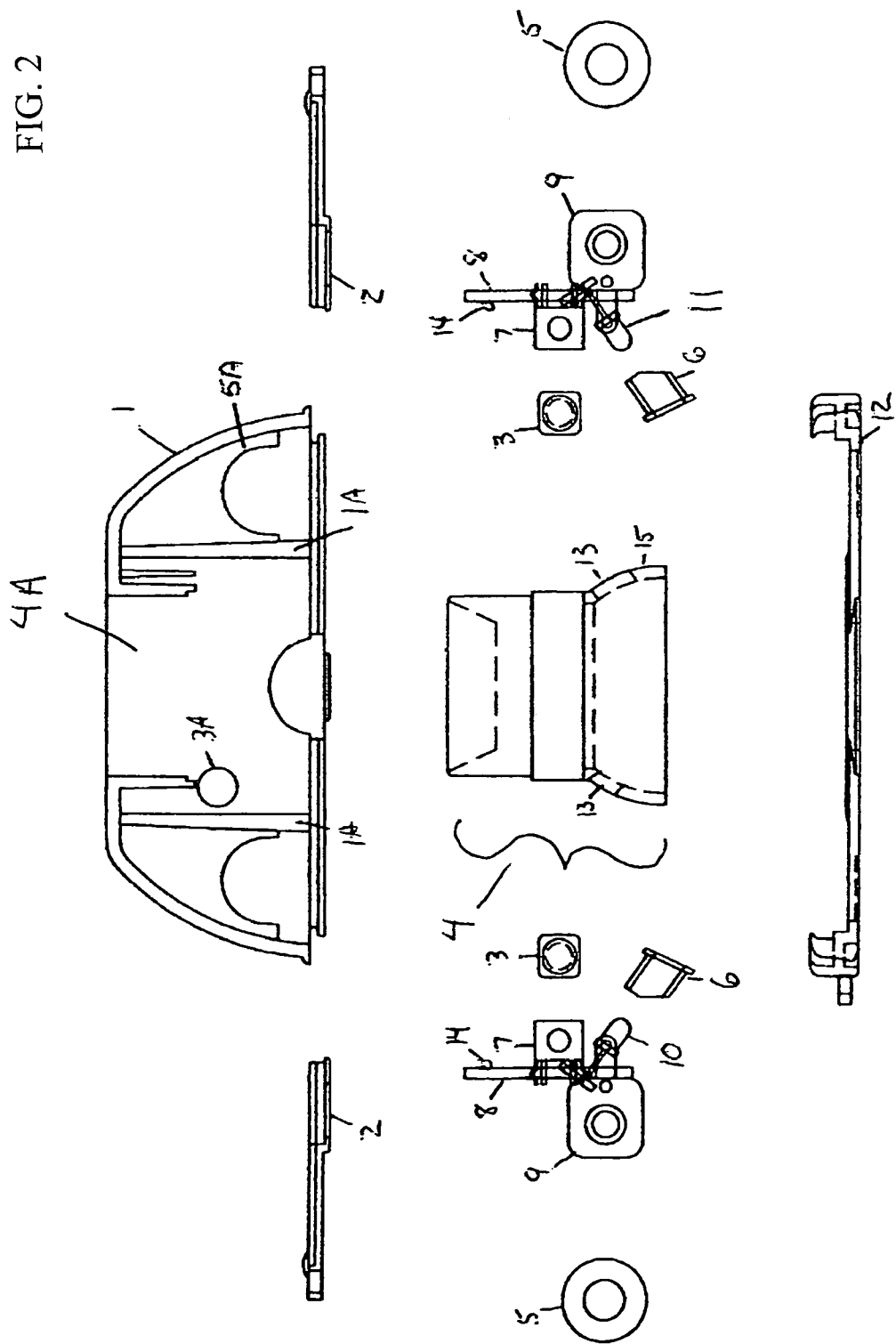

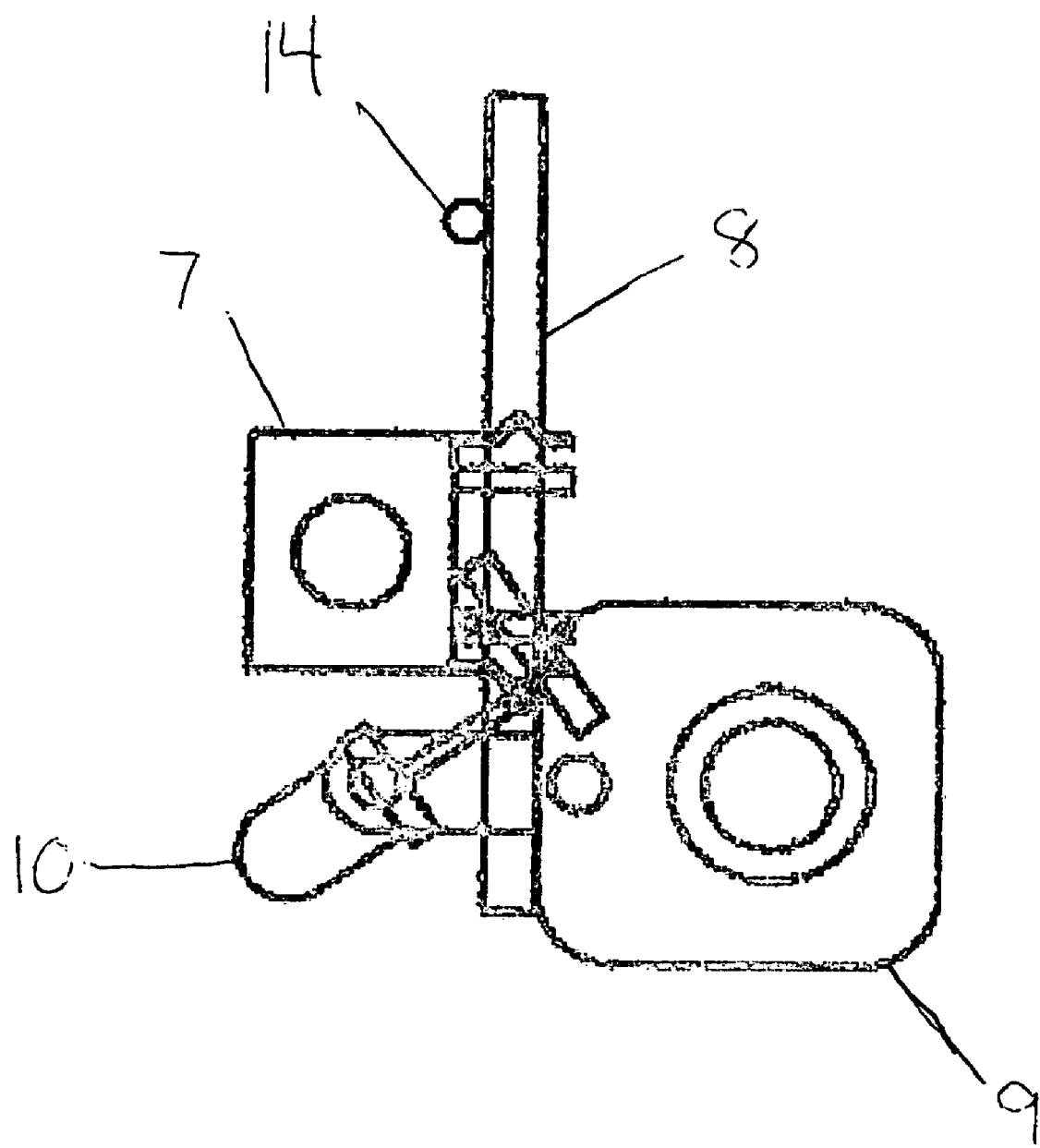

Fig 2C
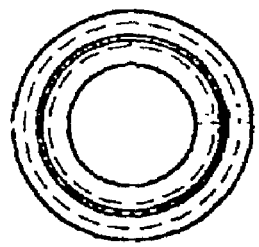
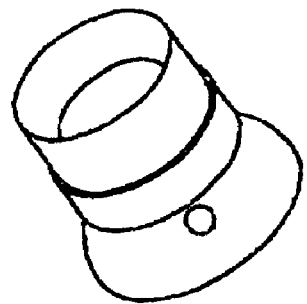
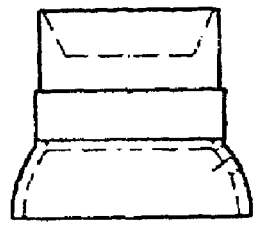
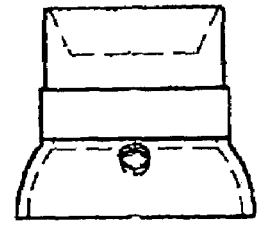

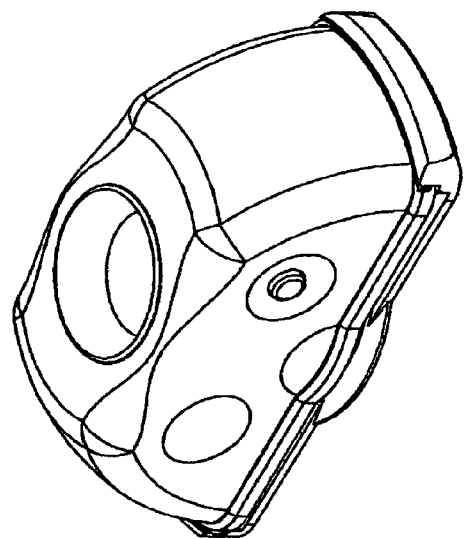
Fig 1B
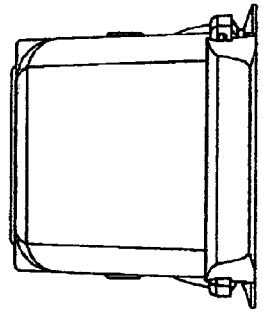
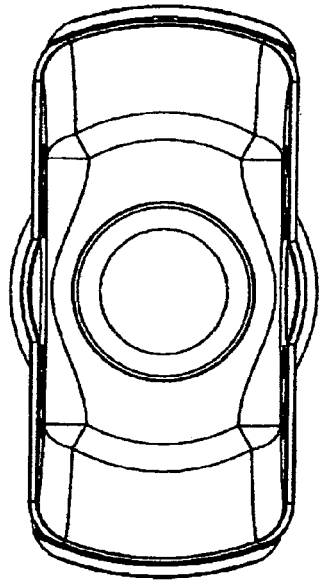
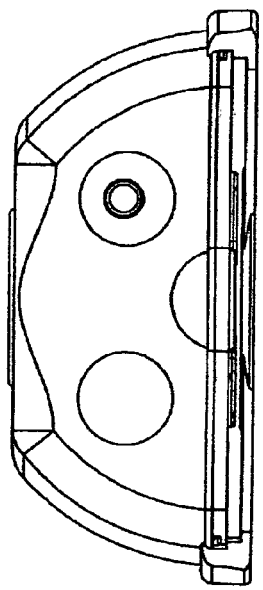

FAKE ID FINDER

CROSS-REFERENCE TO RELATED APPLICATIONS

Applicant claim the priority benefits of U.S. provisional patent application No. 60/906,377 filed on Mar. 12, 2007.

BACKGROUND OF THE INVENTION

Field of the Invention

The present invention relates to the detection and inspection of security features within a driver's license. The US Federal Government has mandated that by the end of 2008 all drivers' licenses should possess a certain level of security features so as to meet federal standards. The advent of inexpensive computer and color printing and copying systems has made counterfeiting a much easier task than heretofore possible. As such the US Government and local states have added higher security features to help prevent counterfeit drivers' licenses, better known as Fake IDs. These security features range from UV to Micro Printing, Optical Variable, Kintegram and Micro printing to name a few. Although there are a number of means such as ultraviolet lamps and illuminated magnifiers which can be used to inspect security features either individually or in combination, none provide the ability to inspect security features in a very compact low cost device that can either be fixed mounted to a wall or hand held. Furthermore, none provide the ability to view UV security features in direct sunlight or act as either a Ultra Violet or white light flashlight at night or in dimly lighted areas.

The present invention creates a dark enclosure so that Ultra Violet light can be used to conduct an inspection outside during daylight hours. Consequently, the present invention is a valuable tool for police law enforcement officers, because it enables the detection of Ultra Violet security features used to asses the validity of a driver's license, outside during daylight hours. The present Invention will work on all US drivers' licenses, as well as and many foreign licenses.

SUMMARY OF THE INVENTION

An object of the present invention is to provide a device to magnify a driver's license sufficiently to view the micro printing, nano printing and Ultra Violet features for fine detailed inspection. Another object is to provide a device that can be used as a flashlight or Ultra Violet flashlight. One other object is to provide a fixed or wall mounted device that can also be hand held. The present invention provides a means for positioning a driver's license at a fixed focal point for optimal magnification and clarity.

The present Invention comprises of a loupe with a minimum of 15× magnification to create a magnified in-focus image while providing a light source within the visible and non visible light spectrum to illuminate the driver's license for detection of micro printing and UV magnification.

The microprint can be hidden anywhere on the driver's license. For instance, in Michigan the micro printing is within the bridge, in Massachusetts and Maine it is under the state's header. Ultra Violet security features can also be located anywhere on a driver's license, and can vary from single to multiple colors, as well as simple text to a portrait of the holder of a driver's license. An additional feature of the present invention is a driver's license guide plate that ensures a proper focal point is attained between the lens and the driver's license for optimal clarity and resolution. Other objects of the present invention will become apparent to those skilled in the art and are in light of the following drawings and detailed description of the invention.

BRIEF DESCRIPTION OF THE DRAWINGS

For a fuller understanding of the nature and object of the present invention, reference is made to the accompanying drawings, wherein:

FIG. 2 shows an exploded view of the invention.

FIG. 2b shows the circuit board.

FIG. 2c shows the loupe.

FIG. 5 shows an assembled view of the instant invention horizontally positioned.

FIG. 12 shows multiple views of the present invention.

DETAILED DESCRIPTION OF ILLUSTRATED EMBODIMENTS AND BEST MODE

The illustrated FIGS. 1 through 12 are herein referenced to depict the various features of the present invention. FIGS. 1a and 1b depict a facsimile of a driver's license. 16 depicts an area where most drivers' licenses add the text for their given state. Micro printing can be located anywhere on the driver's license, front or back 19 points to a location that micro printing may be found. Said micro printing is approximately 0.2 millimeters or 0.008 inches high. It will be recognized by those skilled in the art that magnification of this feature is essential for recognition. Key locations for most micro printing are as follows around the perimeter of the license, around the state seal usually in the right hand corner, down the middle of the license, below the header under the state name in text, on the back shaped as the state; Michigan has their micro printing in the bridge. Thus, while it seems states have several options for placing micro printing, in actuality said micro printing can be placed anywhere on the license.

Figure 1A:
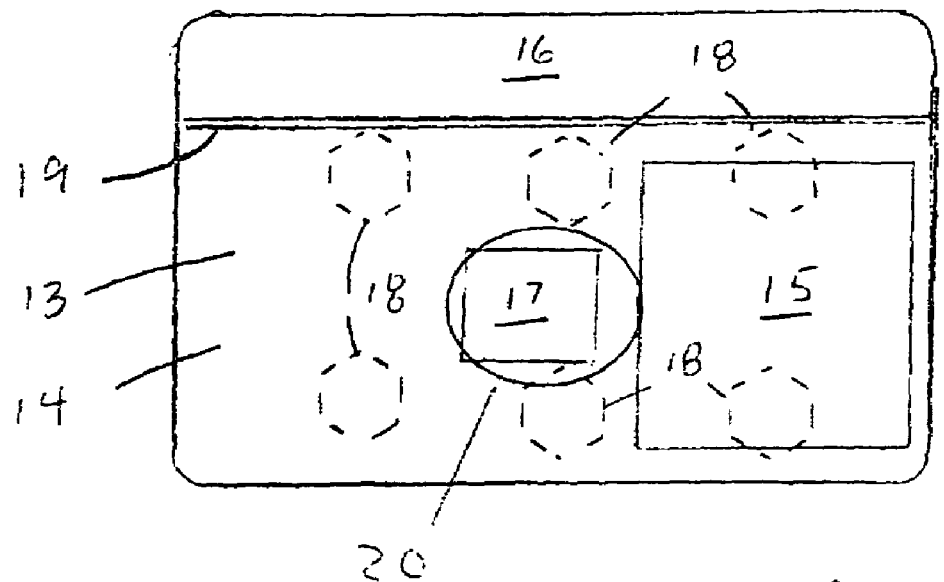
FIG. 1a shows examples of locations of security features of interest on the front of a driver's license.
Figure 1B:
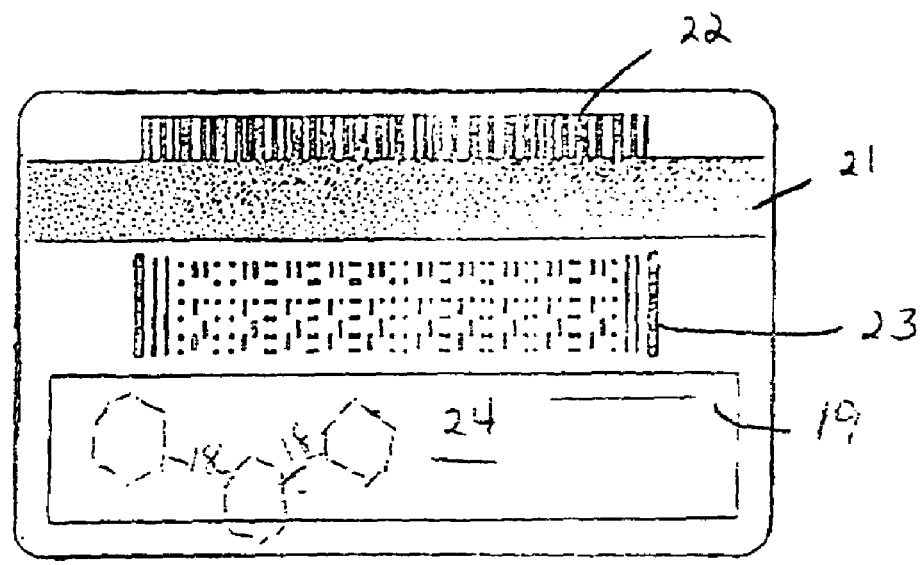
FIG. 1b shows examples of locations of security features of interest on the back of a driver's license.

FIGS. 1a and 1b also show that both micro printing and Ultra Violet can be located on front or back of the license 18 depicts different locations where Ultra Violet can be found, and the same can be said with Ultra Violet security features, namely that they can be found anywhere on the driver's license and be of any shape, from simple letters to a portrait of the license holder. Said features can also come in single to multiple color combinations. FIG. 1a also shows a Kintegrams 20 which can have ultra small micro printing within it, and can only be read clearly with a minimum of 15 magnifications. The Massachusetts Kintegram has ultra small micro printing in the head, legs and arms of the state seal, in which an Indian is holding a bow. Looking at the back of a license it could have a mag strip 21, linear bar code 22 or pdf417 code 23. The bottom of the license 24 depicts where a change of address sticker may be placed. On the front of the license 15 and 17 depict where the picture of the license holder may be placed. Name, address, and licensee number may be placed in the area of 13 and 14 on most licenses.

Figure 3:
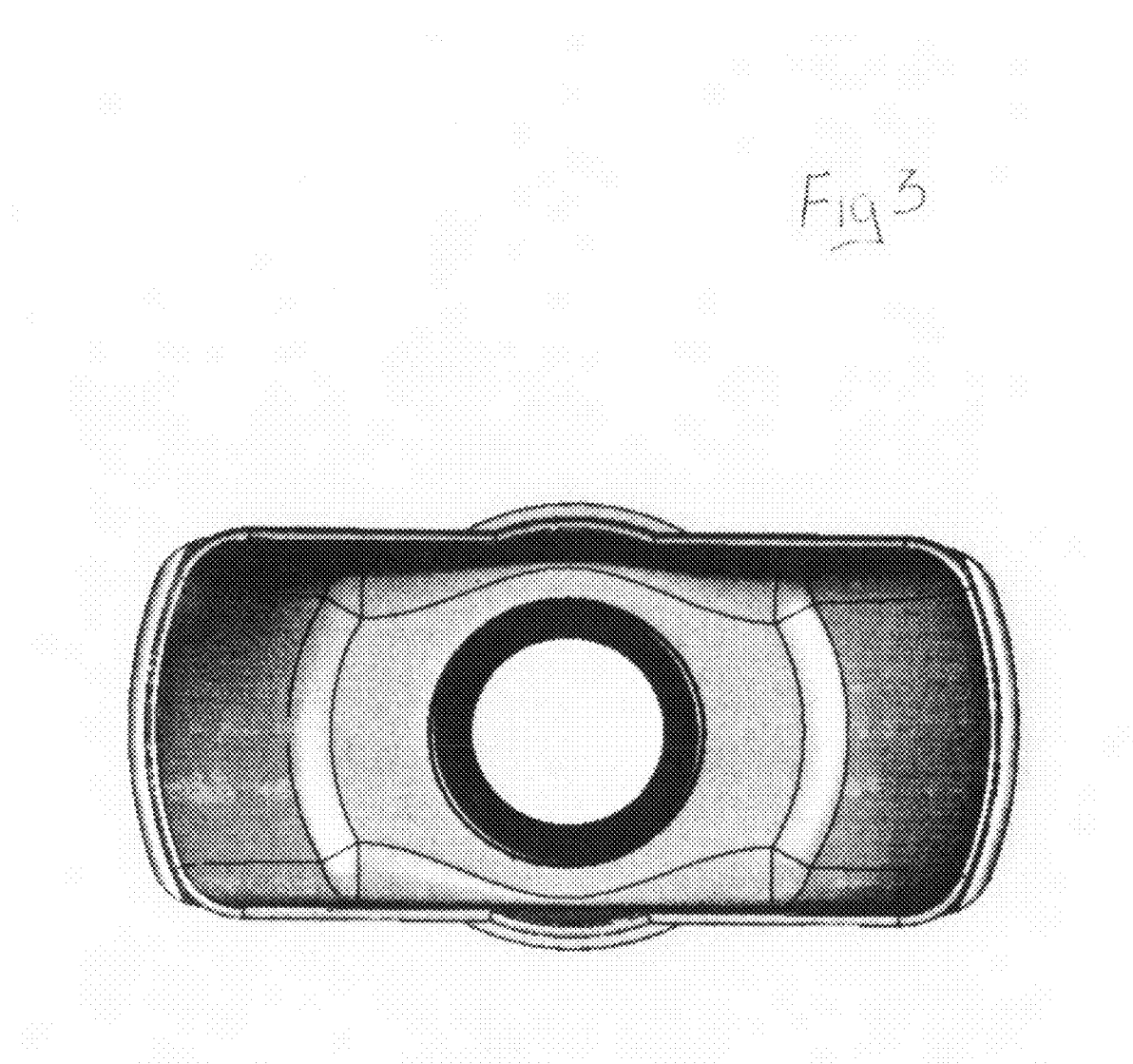
FIG. 3 shows an assembled view of the invention from the top.
Figure 4:
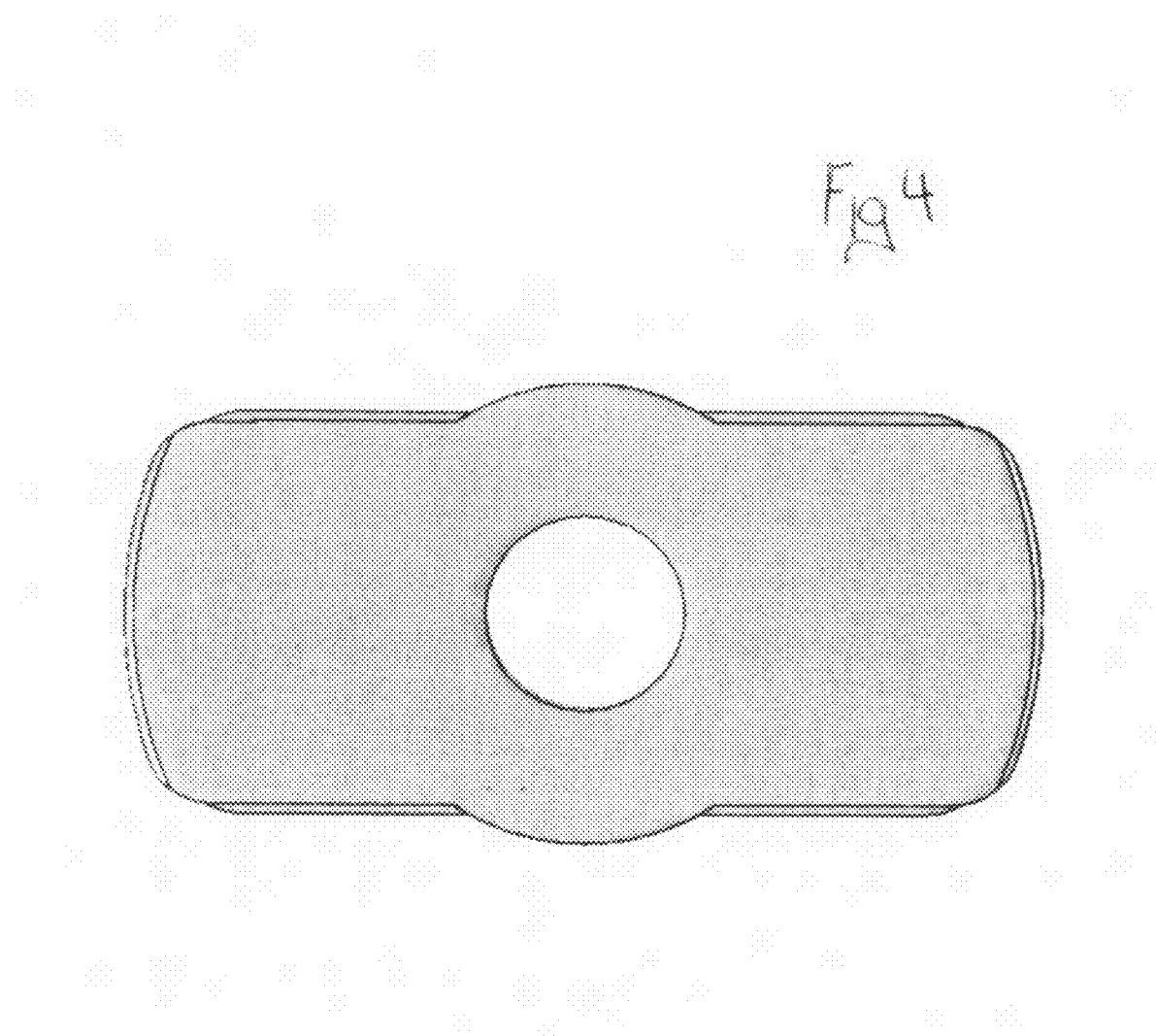
FIG. 4 shows an assembled view of the invention from the bottom.
Figure 7:
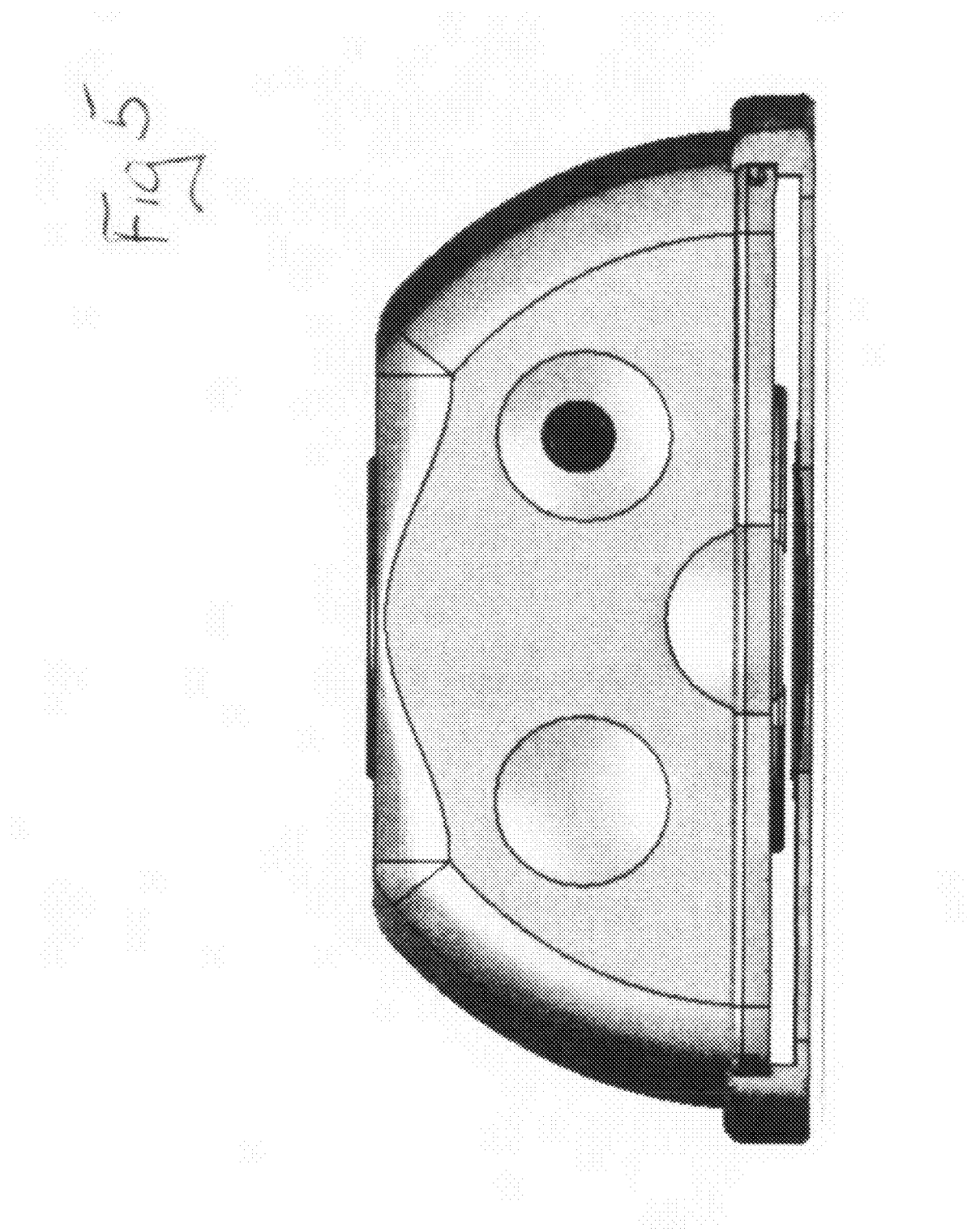
FIG. 7 shows an angled side view of the invention.
Figure 6:
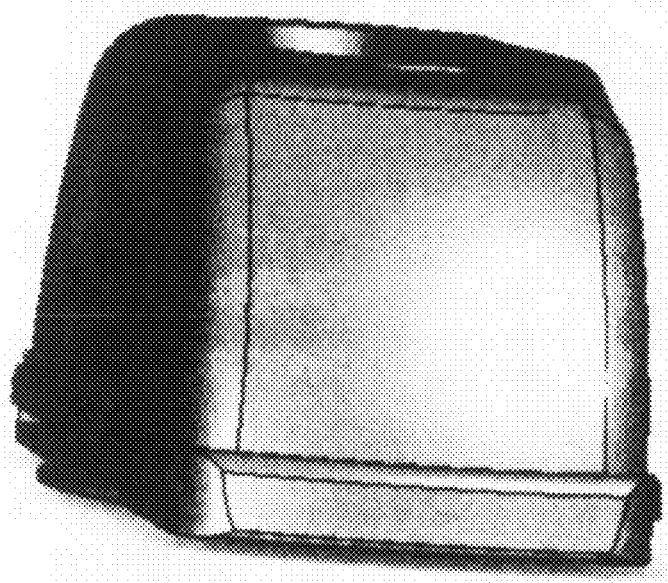
FIG. 6 shows an assembled view of the invention from the front.
Figure 7:
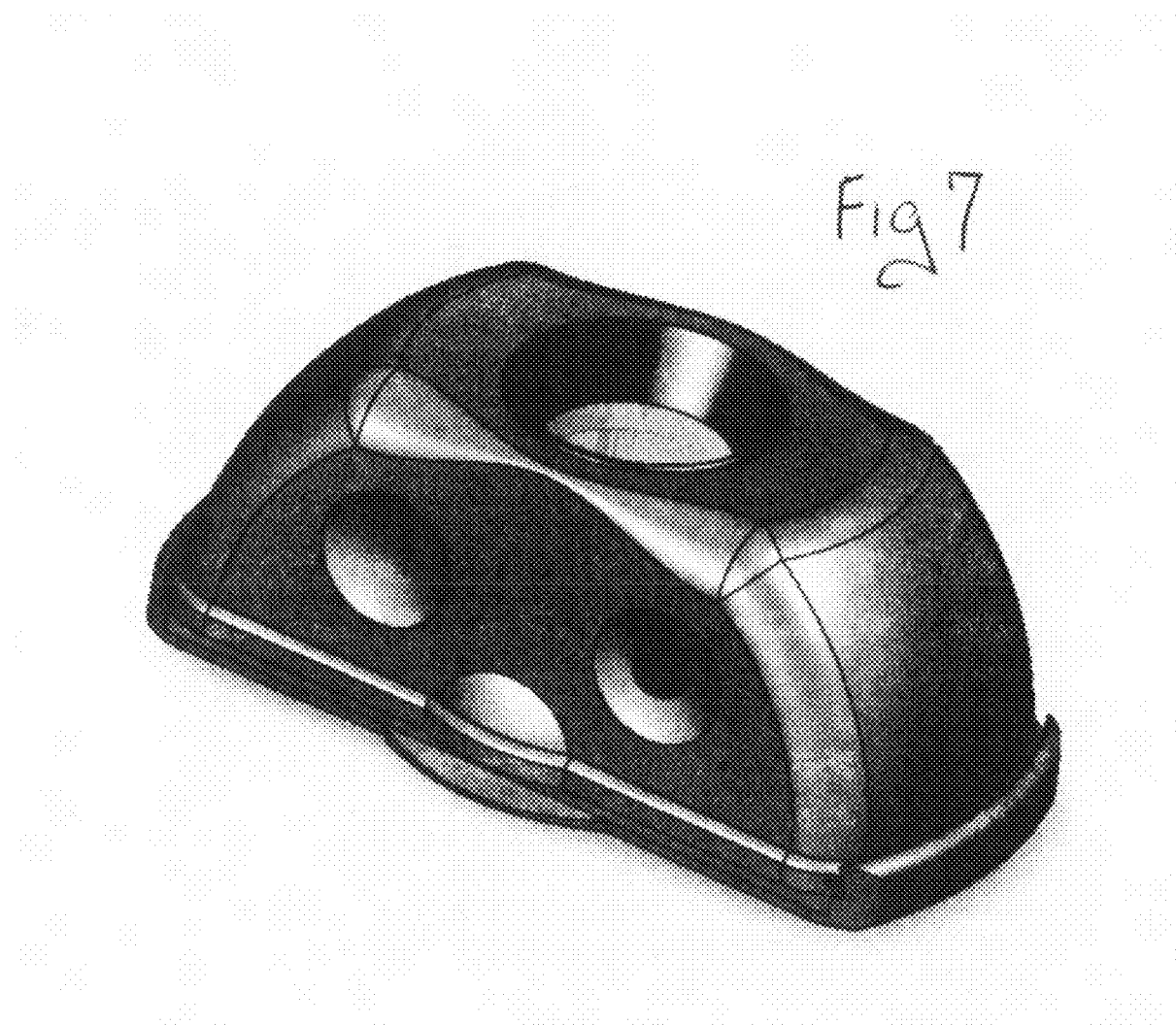

FIG. 2 depicts an exploded view of the invention. The housing 1 holds all the components of the present invention. The housing 1 is designed so that all components snap into place. There are no nuts, screws, or bolts holding the components in place. FIG. 3 shows the circuit boards which consist of a tactile switch 7, circuit board 8, battery connectors 9, resistor 14, Ultra Violet LED 10, and White LED 11. In order to insert the circuit board into the housing, first you would first insert the button 3 is inserted into the housing 1 and then into 3a, then the circuit board is slid into 1a, whose groove holds the circuit board securely in place. The batteries 5 are placed into their groove 5a and are engaged with battery connectors 9. The loupe 4 is inserted through the middle of the housing 1 and snaps into place 4a. The LEDs 10 and 11 are inserted through the holes in the loupe housing 13 and then the grommets 6 are inserted in the inside of the housing of the loupe 15 then into the holes of the loupe 13. The doors are then inserted to lock the batteries 5 and the circuit boards into place. To activate the present invention the button 3 would be depressed which would engage the tactile switch which would send the proper electrical current to the LED 10 or 11. To turn off the LED 10 or 11 just lift your finger from the tactile switch.

The license guide plate 12 is snapped onto the housing 1 and delivers the optimum focal point from the lenses to the drivers license FIGS. 1a and 1b. The license guide plate 12 can be fixed mounted to a wall or any surface, angle or height as desired. The license guide plate 12 has an opening on the bottom to allow the Ultra Violet and white light to pass through. This allows the present invention to be used as a flash light or an Ultra Violet flashlight.

Figure 8:
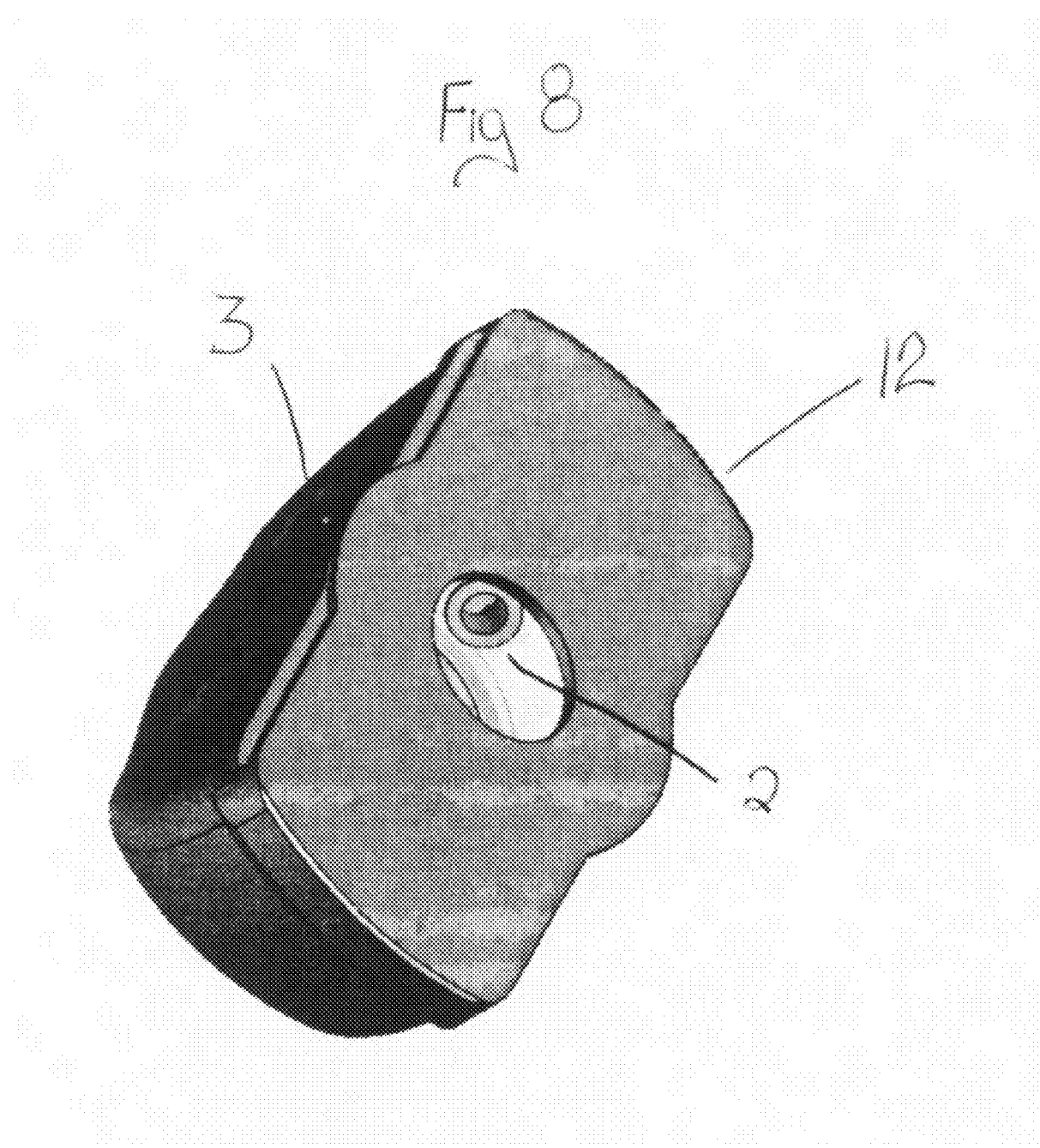
FIG. 8 shows an angled bottom view of the invention.
Figure 9:
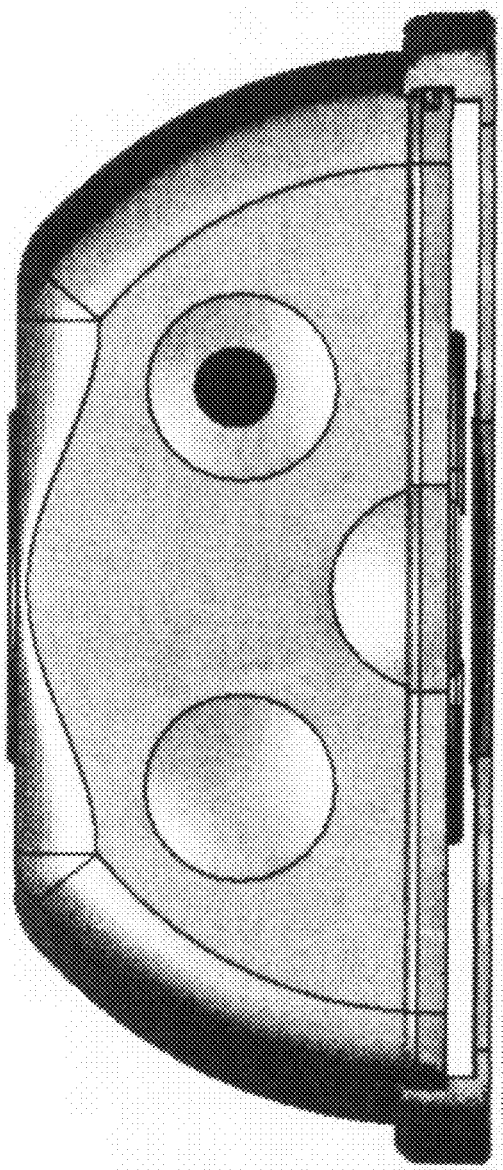
FIG. 9 shows a vertical view of the invention.

FIG. 8 shows why the opening 2 in the license guide plate 12 is important. This opening allows the unit, when used as a hand held device to act as a flashlight or Ultra Violet flashlight. Nothing blocks the light from passing through the opening in the license guide plate 12. This allows for illuminating a driver's license or inspecting the Ultra Violet features at their normal size depending on which button is pressed 3.

Figure 10:
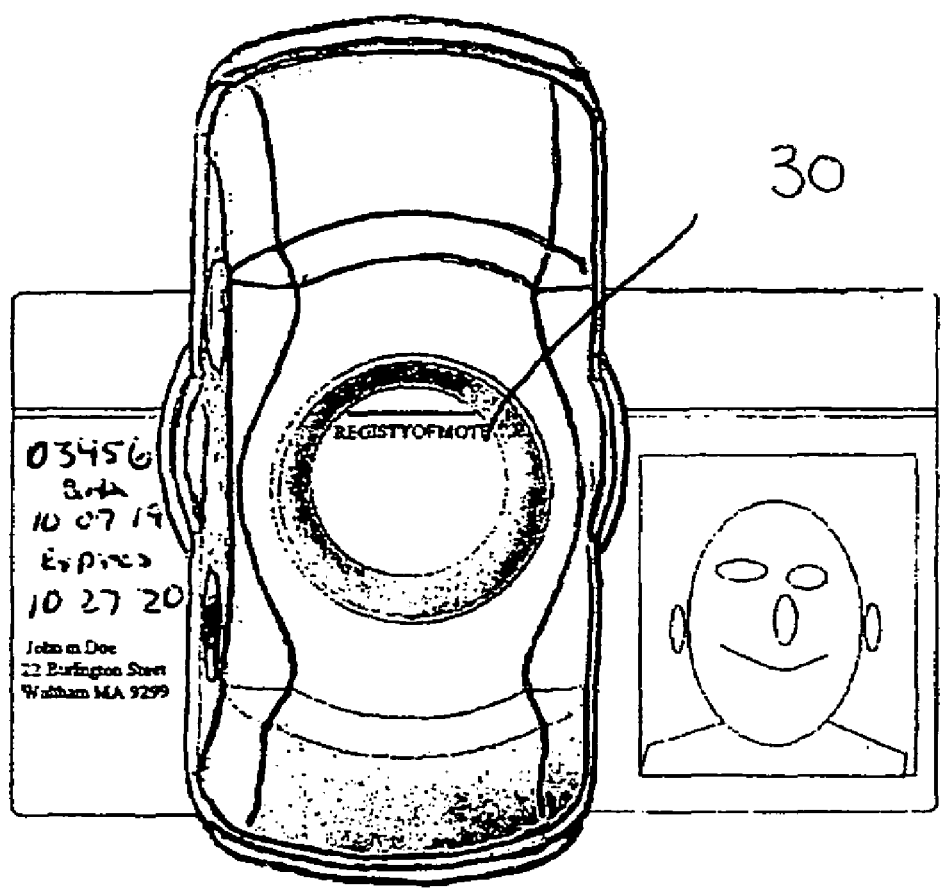
FIG. 10 shows vertical view of driver's license slid through the license guide plate for micro printing detection or UV magnified for a detailed inspection of it.
Figure 11:
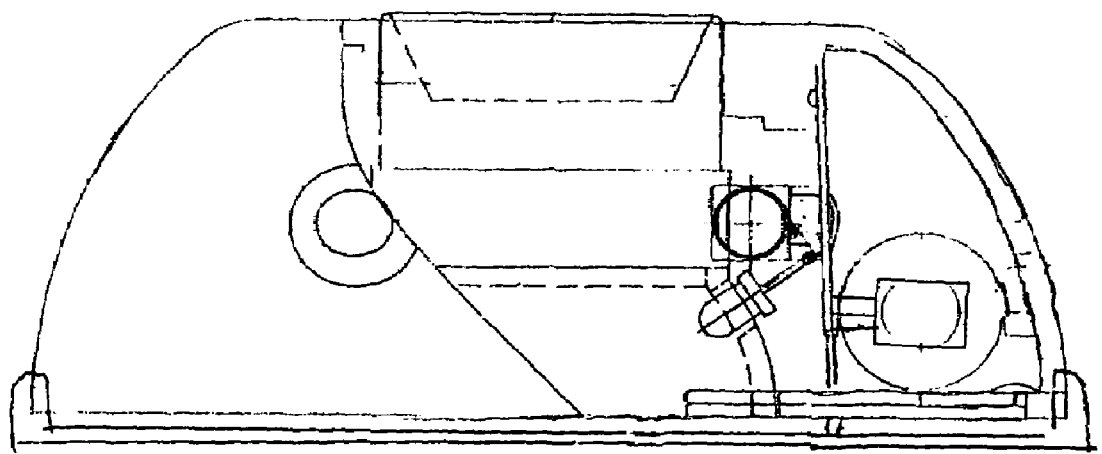
FIG. 11 shows an open look at the assembly of the invention.

FIG. 10 shows a license being slid through the license guide plate. When the white LED button is pressed the micro printing 30 will be at an optimal focal point and clearly readable. If the UV button is pressed, the Ultra Violet feature will be magnified and viewable for detailed inspection.

In summary, the present invention discloses a counterfeit detection device that is useful for optically examining the security features of Drivers Licenses to determine its authenticity. The apparatus places the driver's license at the optimum focal point of a loupe suitable for enlarging the image of the micro printing as well as examining other fine security features such as UV and Kintegrams. In one embodiment, the devise consists of a 10-20 magnification device known as a loupe. One UV led and one white led which are mounted through the housing of the loupe. The LEDs are positioned one hundred and eighty degrees apart from each other and are positioned downward at am angle to illuminate in the middle of the loupes housing. The LEDs are powered by two separate circuit boards which are powered by 6 volt batteries. The invention consists of main housing which holds one loupe, two circuit boards, two batteries; the devise is designed as to allow the loupe and circuit boards to snap into place without the need of nuts, screws or bolts to hold them in place. Further embodiments include a license guide plate which can be snapped onto the bottom of the housing of the devise. The license guide plate allows for the optimum focal point for viewing the micro printing in a driver license. The guide plate also allows the device to be fix mounted to a wall and be used as a hand held unit. There is a whole located on the bottom of the license guide plate to allow the white Light and UV to pass through which enables it to be used as a flashlight or UV flashlight for inspecting the UV unmagnified.

Having described the invention, what is claimed as new and desired to be secured by Letters Patent is:

1. A device disposed for detection and inspection of a plurality of security features located within a driver's license comprising:
   a housing, wherein the housing includes a pair of grooves;
   a pair of circuit boards, wherein each individual circuit board is disposed to be received within a corresponding groove of the pair of grooves, each individual circuit board further comprising,
   a tactile switch;
   a battery connector;
   a resistor;
   a light-emitting diode;
   a magnification apparatus, wherein the apparatus is disposed to be positioned between the pair of grooves located within the housing; and
   a guide plate, wherein the guide plate is removeably attached to the housing.

2. The device of claim 1, wherein the guide plate includes a substantially circular opening aligned with the magnification apparatus located in the housing.

3. The device of claim 2, wherein the guide plate is disposed to receive an identification card and thereby allow for a substantially optimal focal point for inspecting the plurality of security features located within the identification card.

4. The device of claim 1, wherein the device is removeably attached through the guide plate to a static wall with a venue disposed for usage of the device.

5. The device of claim 1, wherein the pair of light emitting diodes includes an ultra violet and a white light.

6. The device of claim 5, wherein the device is disposed to operate during exposure to light through the use of the ultra violet light-emitting diode.

7. The device of claim 5, wherein the device is disposed to operate during exposure to darkness through the use of the white light light-emitting diode.

8. The device of claim 5, wherein the device is disposed to operate as a flashlight through the use of the white light light-emitting diode.

9. The device of claim 5, wherein the device is disposed to operate as an ultra violet flashlight through the use of the ultra violet light-emitting diode.

10. The device of claim 1, wherein the magnification apparatus is a loupe capable of magnification in the range of ten to twenty times the size of an image.

11. The device of claim 1, wherein the plurality of security features are selected from the group consisting of microprinting, optical variable, kintegram and ultra violet.

12. The device of claim 1, wherein each battery connector is disposed to be in electrical communication with a battery to provide power for the light-emitting diodes.

13. The device of claim 2, wherein the light-emitting diodes are positioned downwardly towards the magnification apparatus to illuminate the identification card.

14. The device of claim 13, wherein the light-emitting diodes are positioned downwardly at an angle towards the magnification apparatus to allow inspection of the microprint contained in both in the kintegram and hologram security markings.

15. The device of claim 1 further including a pair of buttons, wherein a first button is disposed to operate the ultra-violet light-emitting diode, and a second button is disposed to operate the white light light-emitting diode.

16. The device of claim 1, wherein the housing further includes a removeably attached base, the base having a pair of slideable opposing pieces disposed to create a substantially circular opening aligned with the magnification apparatus.

* * * * *